United States Patent [19]
Stendahl et al.

[11] Patent Number: 5,955,956
[45] Date of Patent: Sep. 21, 1999

[54] AUDIBLE ALARM SYSTEM FOR AN AUTOMATED EXTERNAL DEFIBRILLATOR

[75] Inventors: Gary B. Stendahl, Crystal; Michael D. Welsch, Woodbury, both of Minn.

[73] Assignee: SurVivaLink Corporation, Minneapolis, Minn.

[21] Appl. No.: 09/057,026

[22] Filed: Apr. 8, 1998

Related U.S. Application Data

[60] Provisional application No. 60/041,809, Apr. 8, 1997.

[51] Int. Cl.[6] .................................................. G08B 21/00
[52] U.S. Cl. .......................... 340/635; 340/637; 340/638; 340/657; 607/5
[58] Field of Search ..................................... 340/635, 637, 340/638, 657; 607/5, 6, 142, 8; 206/438, 701; 327/36

[56] References Cited

U.S. PATENT DOCUMENTS

| 4,158,148 | 6/1979 | Teller, Jr. ................................. 327/36 |
|---|---|---|
| 4,539,562 | 9/1985 | Sanders .................................... 340/657 |
| 4,610,254 | 9/1986 | Morgan et al. .............................. 607/6 |
| 5,464,428 | 11/1995 | Hill .............................................. 607/1 |
| 5,493,278 | 2/1996 | Mackenzie et al. ..................... 340/638 |
| 5,645,571 | 7/1997 | Olson et al. ................................ 607/5 |
| 5,683,423 | 11/1997 | Post .............................................. 607/5 |
| 5,697,955 | 12/1997 | Stolte .......................................... 607/5 |
| 5,792,190 | 8/1998 | Olson et al. ................................ 607/5 |

Primary Examiner—Benjamin C. Lee
Attorney, Agent, or Firm—Patterson & Keough, P.A.

[57] ABSTRACT

The audible alarm system of the present invention incorporates an alarm condition indicator that is designed to detect an alarm condition within the AED. The audible alarm system further incorporates an audible alarm circuit that is connected to the alarm condition indicator and is designed to produce an audible alarm. The audible alarm circuit is initially activated by the alarm condition indicator and then operates independently of the alarm condition after the initial activation.

29 Claims, 6 Drawing Sheets

AUDIBLE ALARM SYSTEM FOR AN AUTOMATED EXTERNAL DEFIBRILLATOR

RELATED APPLICATION

This application claims the benefit of U.S. Provisional Application No. 60/041,809 filed Apr. 8, 1997, the contents of which are herein incorporated by reference and priority to which is claimed under 35 U.S.C. §119(e).

TECHNICAL FIELD

The present invention relates generally to automated external defibrillators. In particular, the present invention is an audible alarm system for an automated external defibrillator wherein the audible alarm system acts to produce an audible alarm through use of an audible alarm circuit. The circuit is initially activated by a processor however, the circuit runs independently of the processor thereafter.

BACKGROUND OF THE INVENTION

Cardiac arrest, exposure to high voltage power lines and other trauma to the body can result in heart fibrillation which is the rapid and uncoordinated contraction of the cardiac muscle. The use of external defibrillators to restore the heartbeat to its normal pace through the application of an electrical shock is a well recognized and important tool for resuscitating patients. External defibrillation is typically used in emergency settings in which the patient is either unconscious or otherwise unable to communicate.

Automated external defibrillators or AEDs are used by police officers, paramedics and other first-responder emergency medical technicians to resuscitate cardiac arrest patients. It is important that the AEDs carried by these technicians be continuously operational and ready for use on a moment's notice. It is essential that in a high stress situation of cardiac arrest, the technician be able to rely on the operability of the AED. Studies have shown that the chances of successfully resuscitating patient decreases approximately ten percent per minute following cardiac arrest. Thus, it is essential that the AED provide an audible alarm to a user when a malfunction or problem with the AED is detected so that the AED may be repaired before its use is required.

Alarm circuits have been known for quite some time now. In many existing devices, alarm circuits may be activated by a watch dog timer or a microprocessor. In some known systems, in order for the alarm circuit to operate, the circuit's real time clock must be continuously operational. Moreover, substantial amounts of additional circuitry are required for the alarm system to operate. In some systems, the alarm circuit is designed to produce an audible alarm at a desired frequency. Each time an audible tone is desired, the circuitry is, in effect, powered up. For devices utilizing batteries having a fixed life, this is a drain on the non-recoverable battery life. There is, therefore, a need for an audible alarm circuit that is capable of producing an audible alarm when initiated by a processor but that may however, run independently of the processor thereafter thereby reducing drain on internal batteries.

SUMMARY OF THE INVENTION

The problems outlined above are in large measure solved by an audible alarm system for an automated external defibrillator (AED) in accordance with the present invention. The audible alarm system of the present invention incorporates an alarm condition indicator that is designed to detect an alarm condition within the AED. The audible alarm system further incorporates an audible alarm circuit that is connected to the alarm condition indicator and is designed to produce an audible alarm. The audible alarm circuit is initially activated by the alarm condition indicator and then operates independently of the alarm condition after the initial activation.

DETAILED DESCRIPTION

Referring to FIG.'s 1–5, an audible alarm system 8 for automated external defibrillators (AEDs) 10 in accordance with the present invention may be appreciated. The audible alarm system 8 generally comprises audible alarm circuit 9 and an alarm condition indicator, such as a processor or watch dog timer. The audible alarm circuit 9 acts to produce an audible alarm when initially activated by an alarm condition indicator however, the audible alarm circuit 9 continues to run independently of the alarm condition indicator after the initial activation.

Figure 1:
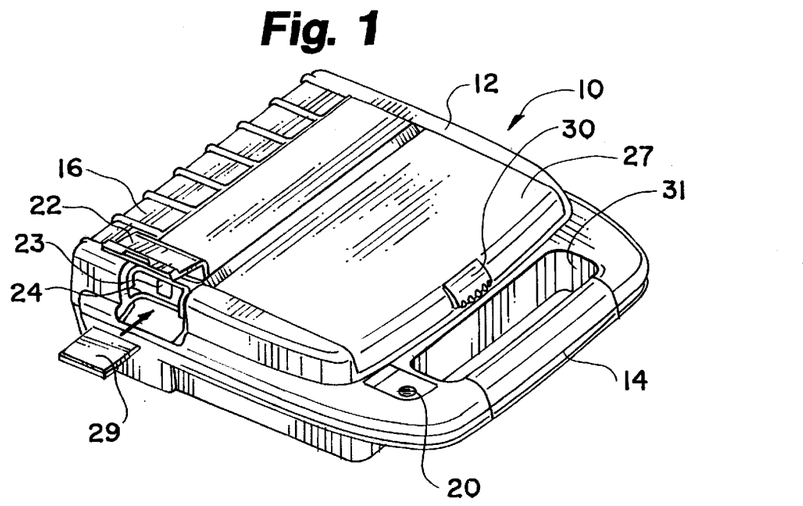
FIG. 1 is a perspective view of an automated external defibrillator (AED) according to the present invention.

As shown AED 10 includes a plastic case 12 with a carrying handle 14 on the front portion. A battery compartment (not visible) in the rear portion of AED 10 encloses a battery pack 16, battery pack 16 being removably disposed within the battery compartment. A visual maintenance indicator 20 and a data access door 22, which conceals a serial connector port 23 and a data card slot 24, are located on the outside of case 12 for easy access by an operator.

Case 12 also includes an electrode compartment 26 defined in the top portion of case 12. A resume/rescue switch 18 (depicted in FIG. 2) is disposed adjacent to electrode compartment 26. Electrode compartment 26 is enclosed by lid 27 which is mounted to case 12 by hinges (not visible). Lid 27 covers resume/rescue switch 18 when lid 27 is in the closed disposition, as depicted in FIG. 1. Resume/rescue switch 18 is actually a single switch with illuminatable labels alternatively indicating the "resume" or the "rescue" function, "rescue" appearing above switch 18 and "resume" appearing below switch 18, depending on whether AED 10 is cuing the operator to perform a rescue or resume operation by activating switch 18.

Figure 2:
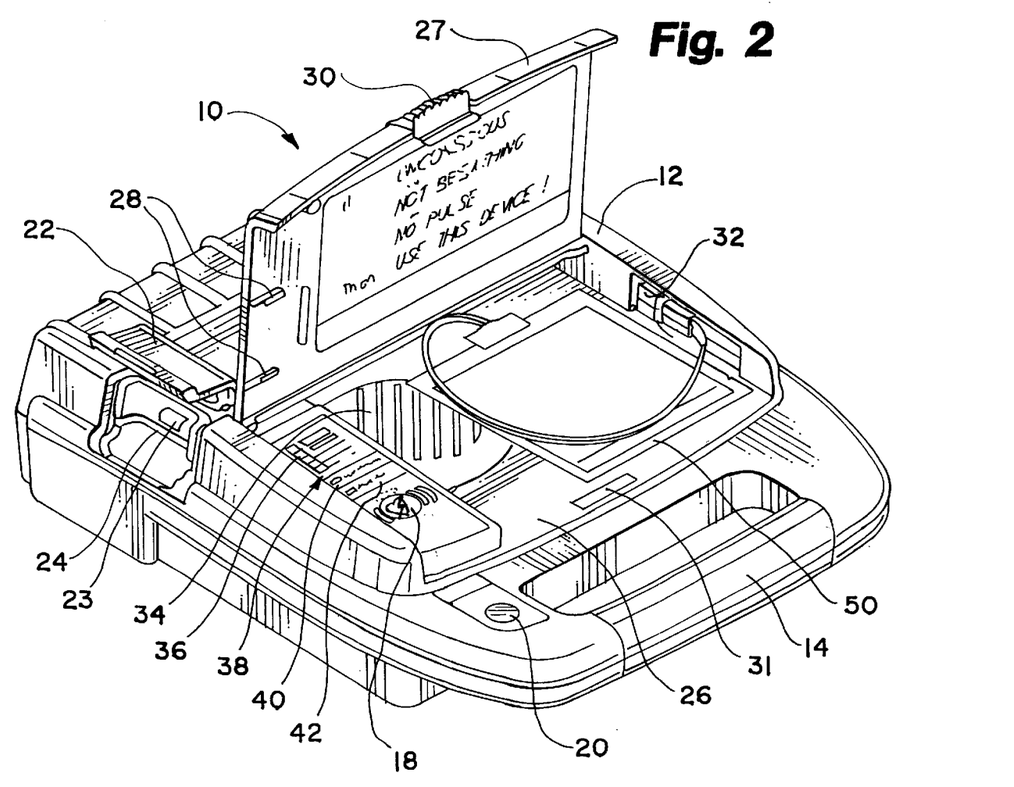
FIG. 2 is a perspective view of the AED of FIG. 1 having the lid open.

The inside of lid 27 incorporates a data card storage clasp 28 for holding a data card 29. A bayonet-type releasable latch 30 holds lid 27 closed when AED 10 is not in use by engaging a receiving recess 31 defined in the floor of electrode compartment 26. Lid 27 is opened by grasping the underside of latch 30, pushing in to disengage latch 30 from recess 31 and lifting upward on latch 30 to gain access to electrode compartment 26.

Figure 3:
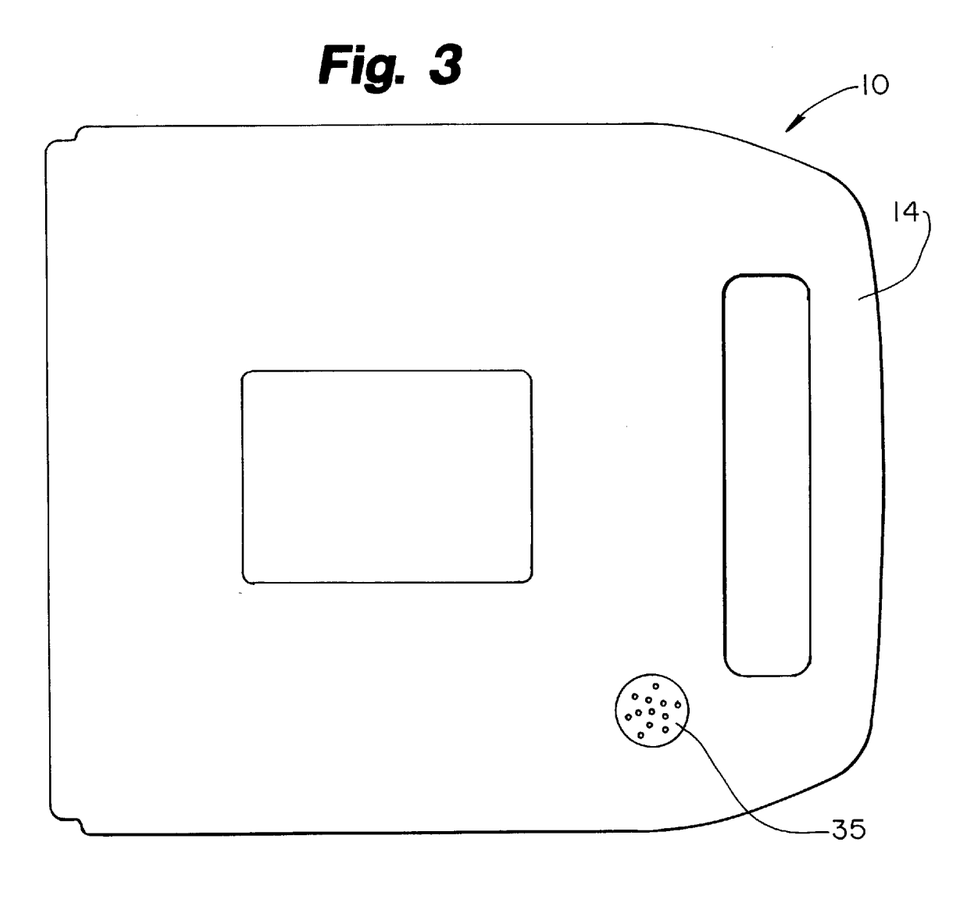
FIG. 3 is a bottom plan view of the AED of FIG. 1.

An electrode connector 32, speaker 34 and diagnostic display panel 36 are disposed on case 12 within electrode compartment 26. Note that in addition to speaker 34, an audible alarm port 35, shown in FIG. 3, is provided on the bottom of AED 19 to permit an audible alarm to be sounded and not muffled when lid 27 is closed. Diagnostic display panel 36 is disposed adjacent to the illuminatable resume/ rescue switch 18. Diagnostic display panel 36 includes visual "Battery Status" indicator light 38, "Electrodes" indicator light 40, and "Service" indicator light 42. An instruction and safety label is located in the inside surface of lid 27. Electrodes 50 are removably connected to electrode connector 32. Electrodes 50 typically include a pair of electrodes for attachment to a patient in a sealed package.

Figure 4:
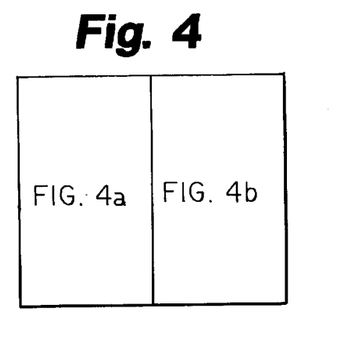
FIG. 4 is a block diagram of an electrical system of the AED shown in FIG.'s 1–3.
Figure 4A:
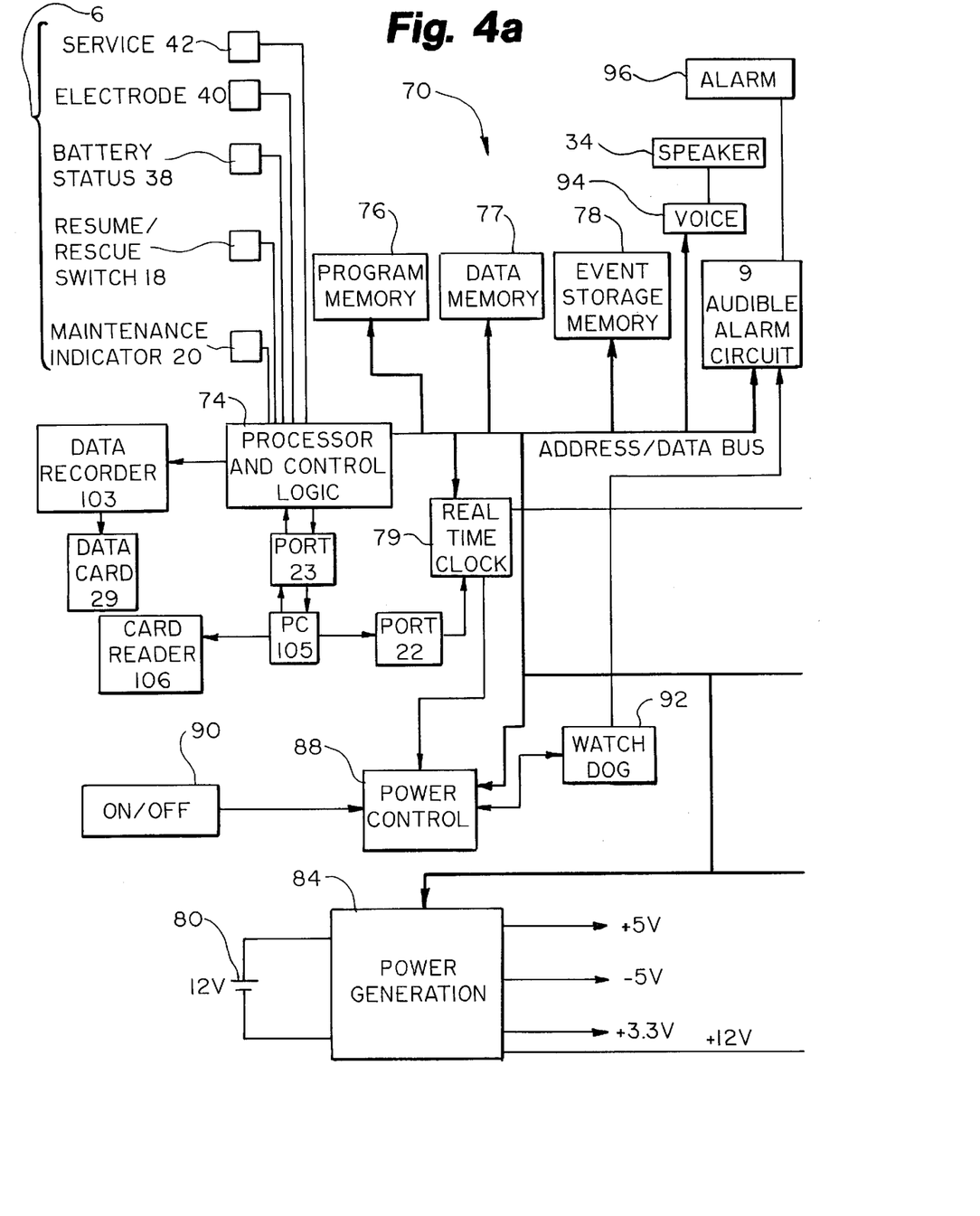
Figure 4B:
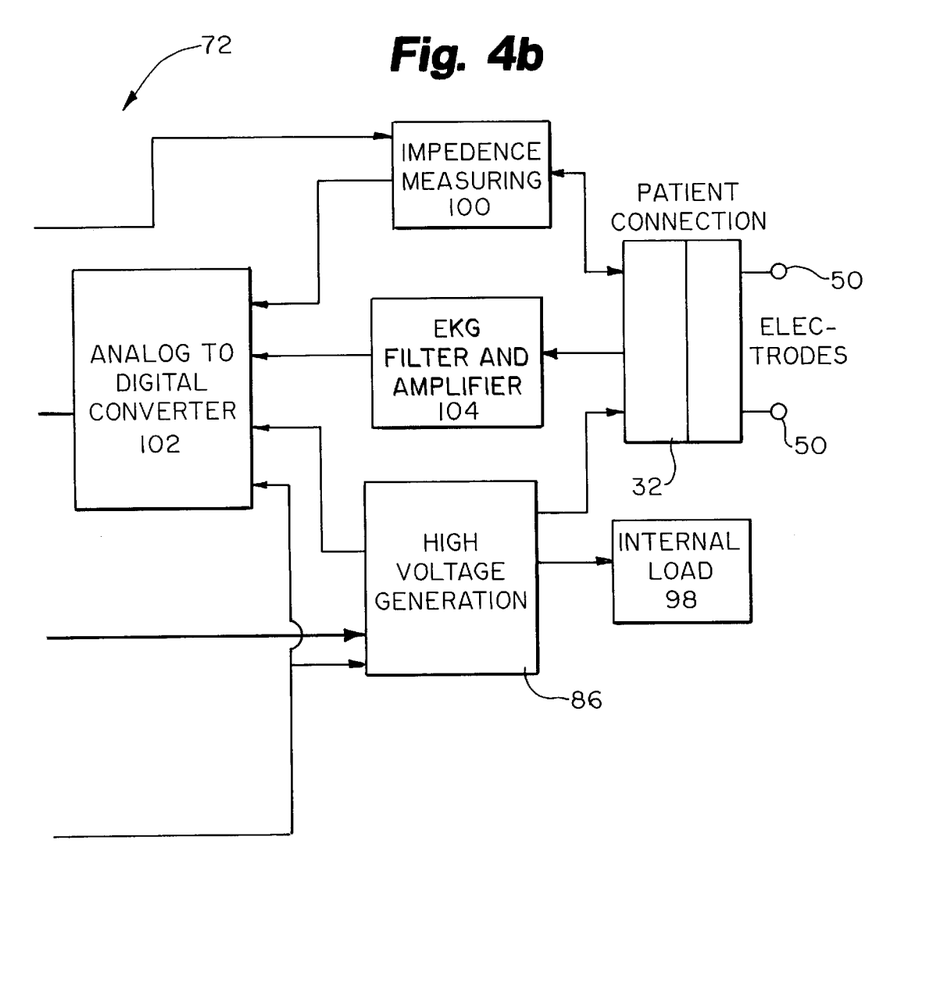

FIG. 4 is a block diagram of the electrical system 70 of AED 10 and depicts audible alarm circuit 9 relative the other components of system 70. The overall operation of AED 10 is controlled by a digital microprocessor-based control system 72 which includes a processor 74 interfaced to program memory 76, data memory 77, event memory 78 and real time clock 79. The operating program executed by processor 74 is stored in program memory 76. Data memory 77 is used by processor 74 as a scratch pad memory during the execution of the operating program.

Electrical power is preferably provided by a lithium sulphur dioxide battery 80 which is enclosed in battery pack 16, battery pack 16 being removably positioned within the battery compartment. Battery 80 may be comprised of a plurality of battery cells that are electrically coupled together. Battery 80 is connected to power generation circuit 84. The "Battery Status" indicator light 38 indicates the charge status of battery 80 and prompts the operator to replace battery 80 when needed.

During normal operation, power generation circuit 84 generates a 12 V supply and regulated 3.3 V and ±5 V supplies with the power provided by battery 80. The 3.3 V supply is generally used to power audible alarm circuit 9, real time clock 79, lid switch 90 and watch dog timer 92 when lid 27 is closed, or in other words, when AED 10 is in a stand-by mode. The +5 V output of power generation circuit 84 functions as a back-up battery to power components of electrical system 70 during the execution of self-tests and to activate maintenance indicators and alarms (as described below). Although not separately shown in FIG. 4, power generation circuit 84 includes voltage level sensing circuits which are coupled to processor 74. The voltage level sensing circuits provide low battery level signals to processor 74.

Power generation circuit 84 is also connected to power control circuit 88 and processor 74. Power control circuit 88 is connected to lid switch 90, watch dog timer 92, real time clock 79 and processor 74. Watch dog timer 92 is also connected to audible alarm circuit 9. Lid switch 90 is a magnetic reed relay switch in one embodiment, and provides signals to processor 74 indicating whether lid 27 is open or closed. Serial connector port 23 is coupled to processor 74 for two-way serial data transfer using an RS-232 protocol. Resume/rescue switch 18 and the "rescue" and "resume" indications thereof, maintenance indicator 20, and "Battery Status" indicator light 38, "Electrodes" indicator light 40, and "Service" indicator light 42 of diagnostic display panel 36, voice circuit 94 and audible alarm circuit 9 are also connected to processor 74. Voice circuit 94 is connected to speaker 34 while audible alarm circuit 9 is connected to piezoelectric audible alarm 96 whose sound is directed out audible alarm port 35. In response to voice prompt control signals from processor 74, circuit 94 and speaker 34 generate audible voice prompts.

High voltage generation circuit 86 is also connected to and controlled by processor 74. High voltage generation circuits such as circuit 86 are generally known and disclosed, for example, in the commonly assigned Persson et al. U.S. Pat. No. 5,405,361, which is hereby incorporated by reference. In response to charge control signals provided by the processor 74, high voltage generation circuit 86 is operated in a charge mode during which one set of semiconductor switches (not separately shown) cause a plurality of capacitors (also not shown), to be charged in parallel to about 400 V each, by power supplied by power generation circuit 84. Once charged, and in response to discharge control signals provided by processor 74, high voltage generation circuit 86 is operated in a discharge mode during which the capacitors are discharged in series by another set of semiconductor switches (not separately shown) to produce the high voltage defibrillation pulses. The defibrillation pulses are applied to the patient through electrode connector 32 which is connected to high voltage generation circuit 86. Under certain circumstances described below, processor 74 causes high voltage generation circuit 86 to be discharged through an internal resistive load 98 rather than connector 32.

Impedance measuring circuit 100 is connected to electrode connector 32 and real time clock 79, and is interfaced to processor 74 through analog-to-digital (A/D) converter 102. The impedance measuring circuit 100 receives a clock signal having a predetermined magnitude from clock 79, and applies the signal to electrodes 50 through connector 32. The magnitude of the clock signal received back from electrodes 50 through connector 32 is monitored by impedance measuring circuit 100. An impedance signal representative of the impedance present across electrode connector 32 is then generated by circuit 100 as a function of the ratio of the magnitudes of the applied and received clock signals (i.e., the attenuation of the applied signal). If the conductive adhesive on electrodes 50 is dried out, if electrodes 50 are not properly connected to connector 32, or if electrodes 50 are not properly positioned on the patient, a relatively high resistance (e.g, greater than about two hundred ohms) will be present across connector 32. The resistance across connector 32 will be between about twenty-five and one hundred eighty ohms when fresh electrodes 50 are properly positioned on the patient with good electrical contacts. The impedance signal representative of the impedance measured by circuit 100 is digitized by A/D converter 102 and provided to processor 74.

AED 10 also includes a data recorder 103 that is interfaced to processor 74 and positioned internally within AED 10 adjacent to data card slot 24 so as to be ready to accept data card 29. AED 10 further includes an electrocardiogram (EKG) filter and amplifier 104 which is connected between electrode connector 32 and A/D converter 102. The EKG or cardiac rhythm of the patient is processed by filter and amplifier 104 in a conventional manner, and digitized by A/D converter 102 before being coupled to processor 74.

The rescue mode operation of AED 10 is initiated when an operator opens lid 27 to access electrodes 50. The opening of lid 27 is detected by lid switch 90, which effectively functions as an on/off switch. In response to this action, power control circuit 88 activates power generation circuit 84 and initiates the rescue mode operation of processor 74. Processor 74 then begins its rescue mode operation by switching maintenance indicator 20 to a maintenance required state (e.g., a yellow visual display in one embodiment), flashing the "rescue" light associated with resume/rescue switch 18 and the indicator lights on diagnostic display panel 36, and performing a lid opened self-test.

During the lid opened self-test, processor 74 checks at least the following: 1) the charge state of battery 80; 2) the interconnection and operability of electrodes 50; 3) the state of event memory 78; 4) the functionality of real time clock 79; and 5) the functionality of A/D converter 102. The charge state of battery 80 is checked by monitoring the voltage level signals provided by power generation circuit 84. If battery 80 is determined to have a low charge, the "battery status" indicator 38 on diagnostic display panel 36 will indicate the sensed status. The interconnection and operability of electrodes 50 are checked by monitoring the impedance signals provided by impedance measuring circuit 100. If electrodes 50 are missing or unplugged from connector 32, or if electrodes 50 are damaged, processor 74 will illuminate "Electrodes" indicator light 40 on diagnostic display panel 36.

Further, during the lid opened self-test, processor 74 accesses event memory 78 to determine whether data from a previous rescue operation are still stored in memory. If so, processor 74 causes the "resume" indicator associated with resume/rescue switch 18 on diagnostic panel 36 to be illuminated, and initiates the generation of a "clear memory" voice prompt. If resume/rescue switch 18 is pressed by the operator following the activation of these indicators, processor 74 clears event memory 78 and proceeds with its rescue mode operation. The functionality of real time clock 79 and A/D converter 102 are checked by monitoring the outputs of these circuit elements for expected signals. Diagnostic display panel "service" light 42 is illuminated by processor 74 if faults are identified in either of real time clock 79 or A/D converter 102.

If the lid opened self-test is successfully completed, processor 74 switches maintenance indicator 20 to an operational state and initiates the rescue mode of operation of AED 10. The rescue mode of operation generates audible voice prompts through speaker 34 to guide the user through the operations of AED 10 and if necessary, delivery of a defibrillation pulse. AED 10 determines its rescue mode steps of operation by monitoring the impedance across electrode connector 32 and by monitoring the patient's cardiac rhythm.

The closing of lid 27 after rescue mode operation activates processor 74 to initiate and perform a lid closed self-test. During the lid closed self-test processor 74 performs a comprehensive check of the status and functionality of AED 10, including: 1) the state of event memory 78; 2) the functionality of real time clock 79; 3) the functionality of A/D converter 102; 4) the functionality of program memory 76, data memory 77 and event memory 78; 5) the charge state of battery 80; and 6) the interconnection and operability of electrodes 50. The state of event memory 78, the state of battery 80, the interconnection and operability of electrodes 50, and the functionality of real time clock 79 and A/D converter 102 are checked in a manner identical to that described above with reference to the lid opened self-test.

Conventional memory test routines are implemented to check the functionality of program memory 76, data memory 77 and event memory 78. Maintenance indicator 20 is switched to its maintenance required state by processor 74 if faults are identified during the lid closed self-test. No audible alarms are actuated if faults are identified in the charge state of battery 80 or the interconnection or functionality of electrodes 50 during the lid closed self-test. However, audible alarm circuit 9 is activated by processor 74 if other faults are identified during the lid closed self-test.

A daily self-test is initiated and performed by processor 74 at a predetermined time each day (i.e., every twenty-four hours). During the daily self-test, processor 74 performs all the component check operations described above that are performed during the lid opened and lid closed self-tests. In addition to illuminating the appropriate lights on diagnostic display panel 36, processor 74 leaves maintenance indicator 20 in its maintenance required state and activates audible alarm circuit 9 if faults are identified during the daily self-test.

Processor 74 also initiates and performs a weekly self-test at a predetermined time one day each week. During the weekly self-test processor 74 performs all the component check operations described above that are performed during the daily self-test. In addition, processor 74 causes high voltage generation circuit 86 to sequentially operate in its charge and discharge modes, with the charge being dumped to an internal resistive load 98. While high voltage generation circuit 86 is operating in the charge mode, processor 74 monitors the time required to charge the circuit's capacitors and the capacitor voltage. A fault is identified if either is out of nominal conditions. Maintenance indicator 20 and audible alarm circuit 9 are actuated in the manner described above if any faults are identified during the weekly self-test. Note that all performed test and patient data may be recorded in event memory 78.

Watch dog timer 92 is set to time watch dog time-out periods of about thirty hours (i.e., a period greater than twenty-four hour periods between daily self-tests), and is reset by processor 74 at the beginning of each daily self-test and each time lid 27 is opened. In the event control system 70 malfunctions and watch dog timer 92 times out, internal hardware switches maintenance indicator 20 to the maintenance required state and processor 74 actuates audible alarm circuit 9 to alert an operator to the fact that AED 10 requires maintenance. Watch dog timer 92 is tied directly to audible alarm circuit 9 such that if a fault with processor 74 itself occurs, watch dog timer 92 can activate audible alarm circuit 9 on its own.

Figure 5:
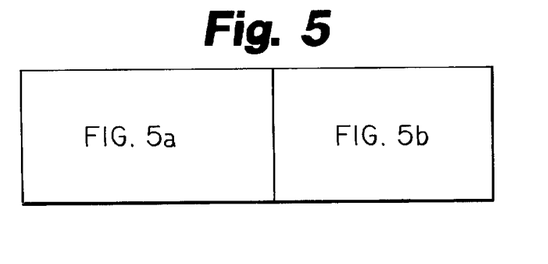
FIG. 5 is schematic diagram of the audible alarm circuit of the present invention.
Figure 5A:
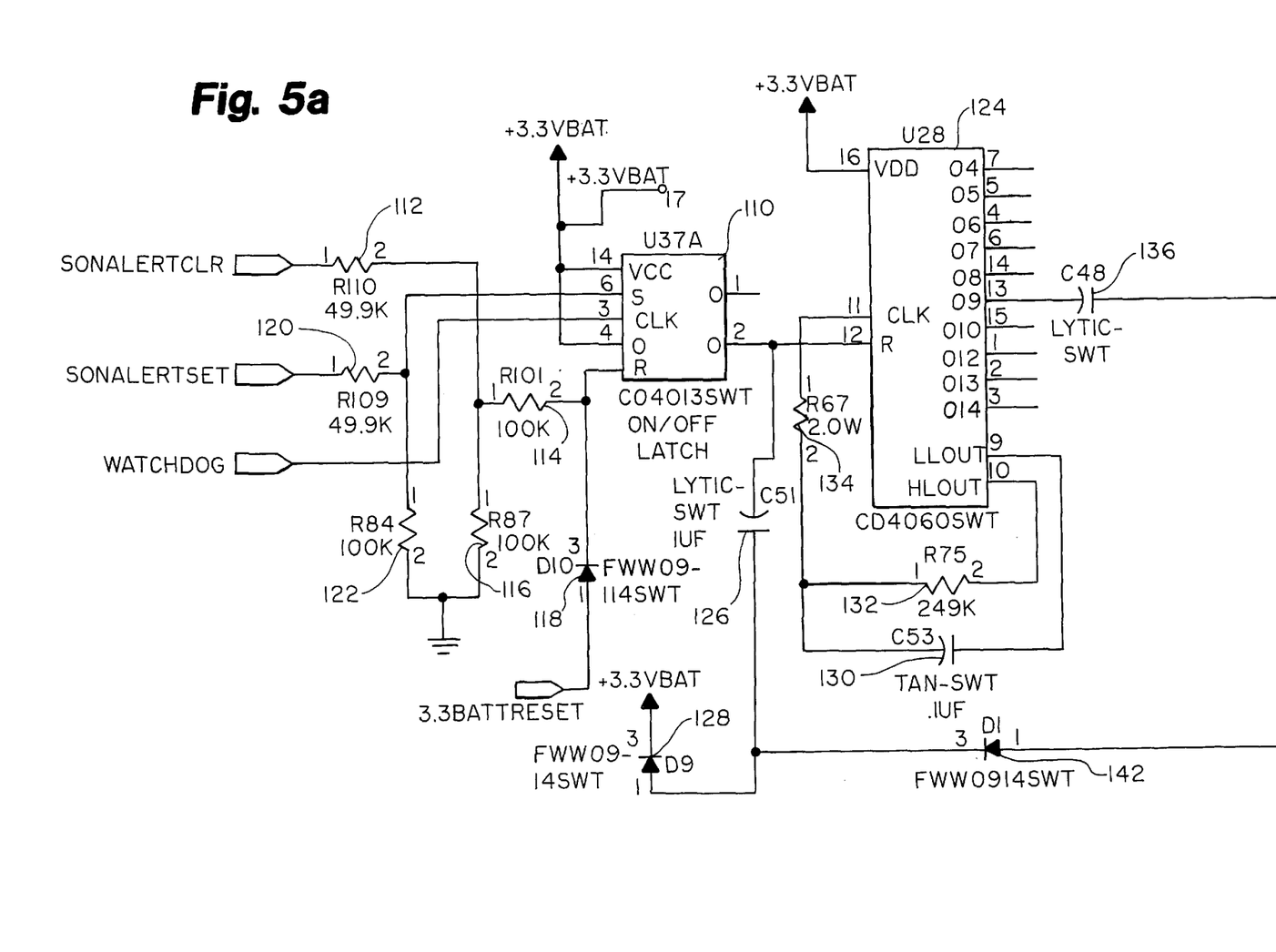
Figure 5B:
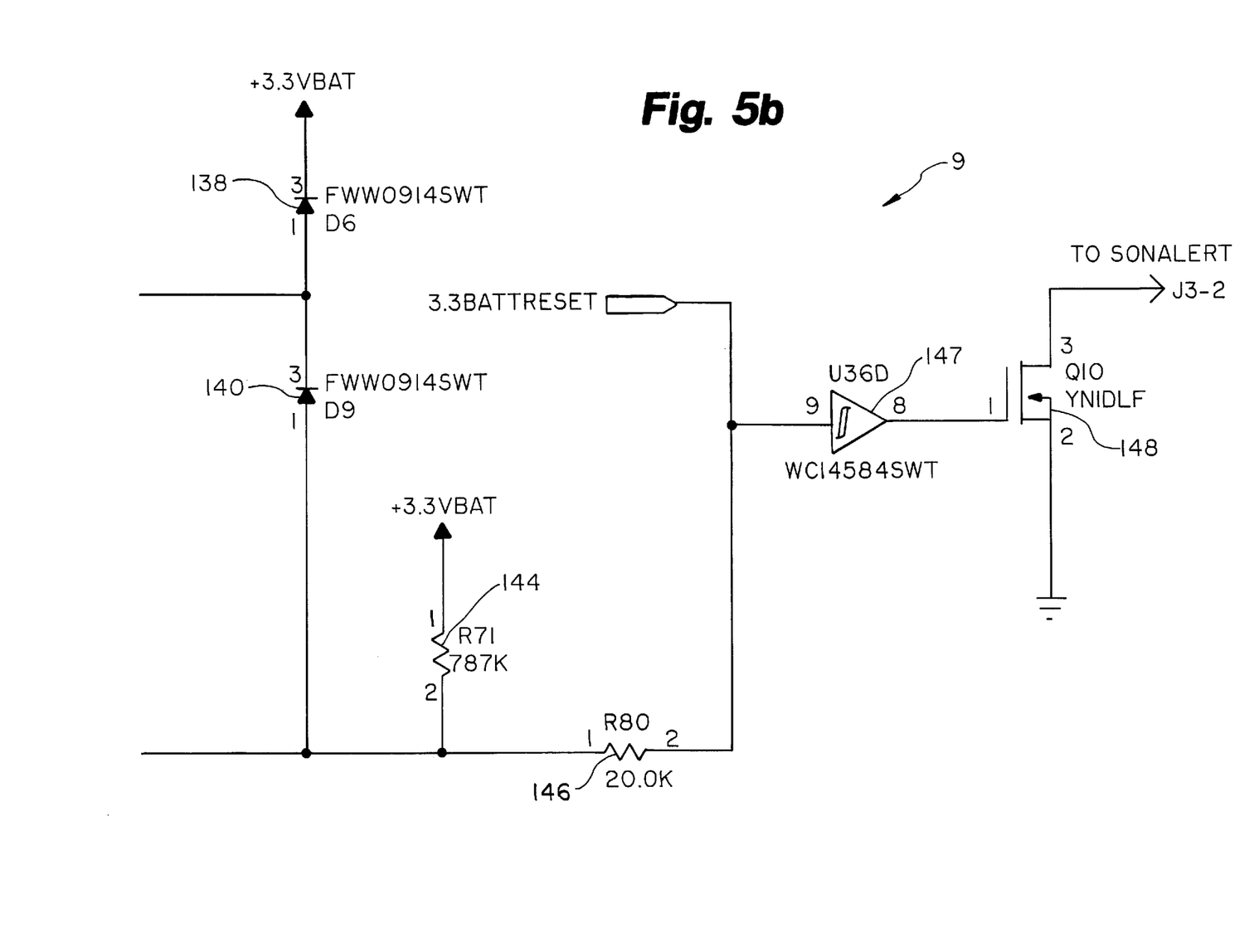

As shown in FIG. 5, audible alarm circuit 9 incorporates a D-type flip-flop 110. An audible alarm circuit clear signal from processor 74, designated "SONALERTCLR", is tied to a resistor 112. Resistor 112 is connected to a resistor 114 and a resistor 116 which is tied to ground. These resistors operate to step down the voltage of the audible alarm circuit clear signal from approximately +5 V to approximately +3.3 volts. Resistor 114 is connected to a diode 118 and to the reset of flip-flop 110. A 3.3 battery reset signal from processor 74 is also connected to diode 118.

An audible alarm circuit set signal from processor 74, designated "SONALERTSET", is coupled to a resistor 120. Resistor 120 is connected to a resistor 122, which is tied to ground, and flip-flop 110. Resistors 120 and 122 operate to step down the voltage of the audible alarm circuit set signal. The output of watch dog timer 92, designated "WATCHDOG", is also tied to flip-flop 110.

The 3.3 volt battery supply powers flip-flop 110 and a fourteen stage ripple binary counter 124. The output of flip-flop 110, designated –Q, is input to ripple counter 124 and is also tied to a capacitor 126. Capacitor 126 is connected to a diode 128 which is connected to the 3.3 volt battery supply. The LLOUT pin of ripple counter 124 is connected to a capacitor 130 while the HLOUT pin of ripple counter 124 is connected to a resistor 132. Both capacitor 130 and resistor 132 are connected to a resistor 134 which is input to the—CLK pin of binary counter 124.

The output of ripple counter 124, designated Q9, is tied to a capacitor 136 which is connected to a diode 138 and a diode 140. Diode 138 is connected to the 3.3 volt battery supply. Diode 140 is connected to yet another diode 142 which is connected to diode 128 and resistors 144 and 146. Resistor 146 is tied to the 3.3 volt battery reset signal from processor 74 and to the input of a Schmitt trigger 147. The output of Schmitt trigger 147 is connected to the gate of a MOSFET 148. The drain of MOSFET 148 is connected to audible alarm 96.

In operation, when a fault or problem is detected by processor 74 or when watch dog timer 92 detects a problem with processor 74 an alarm condition is indicated to audible alarm circuit 9 through the "SONALERTSET" signal or "WATCHDOG" signal, respectively. When either the "SONALERTSET" or "WATCHDOG" are activated high, the high signal sets the flip-flop 110 which in turn pulls flip-flop output –Q low. –Q is normally in the high state. The transition of –Q from a high to low state enables ripple counter 124 and initially activates audible alarm 96. The transition of –Q from high to low activates the audible alarm 96 by pulling the anode of capacitor 126 to ground. This in turn pulls the input to Schmitt trigger 147 low which enables the Schmitt trigger output high turning on audible alarm 96 for a time constant governed by capacitor 126 and resistor 144. The continued sounding of audible alarm 96 is facilitated by the enabled state of binary counter 124. When binary counter 124 is enabled its output Q9 is oscillating at approximately a thirty second rate, the rate is governed by capacitor 130 and resistor 132. When output Q9 transitions low, it pulls the anode of capacitor 136 low which also pulls the input to Schmitt trigger 147 low enabling the output of Schmitt trigger 147 high thereby sounding audible alarm 96 for a time constant governed by capacitor 130 and resistor 144. Attention to the maintenance of AED 10 will reset audible alarm circuit 9 through the "SONALERTCLR" and/or the 3.3 battery reset signals. That is, when the "SONALERTCLR" or 3.3 battery reset signal go high, flip-flop 110 is reset thereby transitioning –Q from a low to high state and turning off audible alarm 96.

Note that once an alarm condition has been indicated, audible alarm circuit 9 takes over providing a continuously sounding alarm and operating independently of processor 74. Thus, although audible alarm circuit 9 is driven by a battery source, the amount of power necessary to drive audible alarm circuit 9 is far less than what is necessary to drive processor 74 and all of its supporting circuitry. Audible alarm circuit 9 operates on very low current creating a very low drain on the battery source. Audible alarm circuit 9 uses piezoelectric audible alarm 96 to generate a warning sound at a desired frequency. The warning sound emits from audible alarm port 35.

The present invention may be embodied in other specific forms without departing from the spirit of the essential attributes thereof; therefore, the illustrated embodiment should be considered in all respects as illustrative and not restrictive, reference being made to the appended claims rather than to the foregoing description to indicate the scope of the invention.

What is claimed:

1. An audible alarm system for an automated external defibrillator (AED), comprising:
   an alarm condition indicator designed to detect an alarm condition within the AED; and
   an audible alarm circuit, operable on a power level of less than 5 volts from a power source wherein said power level is less than the operating power level of the alarm condition indicator from the power source, connected to said alarm condition indicator and designed to produce an audible alarm through an external audible alarm port, said audible alarm circuit initially activated by said alarm condition indicator, and wherein said audible alarm circuit operates independently of said alarm condition indicator after the initial activation.

2. The audible alarm system of claim 1, wherein said alarm condition indicator comprises a processor.

3. The audible alarm system of claim 1, wherein said alarm condition indicator comprises a watch dog timer.

4. The audible alarm system of claim 1, wherein said alarm condition indicator detects said alarm condition during a lid closed self-test.

5. The audible alarm system of claim 1, wherein said alarm condition indicator detects said alarm condition during a periodic self-test.

6. The audible alarm system of claim 5, wherein said alarm condition indicator detect said alarm condition during a daily self-test.

7. The audible alarm system of claim 5, wherein said alarm condition indicator detect said alarm condition during a weekly self-test.

8. The audible alarm system of claim 1, wherein said audible alarm circuit is connected to a speaker.

9. The audible alarm system of claim 1, wherein said audible alarm circuit is connected to a piezoelectric alarm.

10. The audible alarm system of claim 1, wherein said alarm condition is selected from the group consisting of: a processor malfunction, a real-time clock malfunction, an analog-to-digital converter malfunction, a program memory malfunction, a data memory malfunction, an event memory malfunction and a high voltage generation circuit malfunction.

11. The audible alarm system of claim 1, wherein the audible alarm circuit is operable on approximately 3.3 volts.

12. An audible alarm system for an automated external defibrillator (AED), comprising:
   an alarm condition indicator designed to detect an alarm condition within the AED and to require a first amount of power from a power source for operation; and
   an audible alarm circuit designed to produce an audible alarm, said audible alarm circuit coupled to said alarm condition indicator, said audible alarm circuit designed to be initially activated by said alarm condition indicator, operate independently of said alarm condition indicator after the initial activation, and require a second amount of power from the power source for operation that is less than said first amount of power, where said second amount of power requires less than 5 volts.

13. The audible alarm system of claim 12, wherein said alarm condition indicator is a processor.

14. The audible alarm system of claim 12, wherein said alarm condition indicator is a watch dog timer.

15. The audible alarm system of claim 12, wherein said alarm condition indicator detects alarm conditions during a lid closed self-test performed by the AED.

16. The audible alarm system of claim 12, wherein said alarm condition indicator detects alarm conditions during a daily self-test performed by the AED.

17. The audible alarm system of claim 12, wherein said alarm condition indicator detects alarm conditions during a weekly self-test performed by the AED.

18. The audible alarm system of claim 12, wherein said audible alarm circuit is connected to a speaker port formed in the housing of the AED.

19. The audible alarm system of claim 12, wherein said alarm condition is selected from the group consisting of: a processor malfunction, a real-time clock malfunction, an analog-to-digital converter malfunction, a program memory malfunction, a data memory malfunction, an event memory malfunction and a high voltage generation circuit malfunction.

20. The audible alarm system of claim 12, wherein said second amount of power requires approximately 3.3 volts.

21. An audible alarm system for an automated external defibrillator (AED), comprising:

a processor designed to detect an alarm condition within the AED;

a watch dog timer coupled to said processor, said watch dog timer designed to detect a processor alarm condition; and an audible alarm circuit, operable on a power level of less than 5 volts from a power source wherein said power level is less than the operating power level of the processor and the watch dog timer from the power source, designed to produce an audible alarm, said audible alarm circuit coupled to said processor and said watch dog timer, said watch dog timer and said processor designed to initially actuate said audible alarm circuit upon detection of an alarm condition, and wherein said audible alarm circuit operates independently of said processor and said watch dog timer after its initial activation.

22. The audible alarm system of claim 21, wherein a power source is a battery removably mounted to the AED.

23. The audible alarm system of claim 21, wherein said processor is adapted to detect alarm conditions during a lid closed self-test of the AED.

24. The audible alarm system of claim 21, wherein said processor is adapted to detect alarm conditions during a daily self-test of the AED.

25. The audible alarm system of claim 21, wherein said processor is adapted to detect alarm conditions during a weekly self-test of the AED.

26. The audible alarm system of claim 21, wherein said audible alarm circuit is connected to a speaker port formed in a housing of the AED.

27. The audible alarm system of claim 21, wherein said alarm condition is selected from the group consisting of: a processor malfunction, a real-time clock malfunction, an analog-to-digital converter malfunction, a program memory malfunction, a data memory malfunction, an event memory malfunction and a high voltage generation circuit malfunction.

28. The audible alarm system of claim 19, wherein said audible alarm circuit is connected to a piezoelectric alarm.

29. The audible alarm system of claim 21, wherein the audible alarm circuit is operable on approximately 3.3 volts.

* * * * *